United States Patent [19]

Messerschmidt

[11] Patent Number: 4,730,882
[45] Date of Patent: Mar. 15, 1988

[54] MULTIPLE INTERNAL REFLECTANCE SPECTROSCOPY SYSTEM

[75] Inventor: Robert G. Messerschmidt, Westport, Conn.

[73] Assignee: Spectra-Tech, Inc., Stamford, Conn.

[21] Appl. No.: 827,367

[22] Filed: Feb. 10, 1986

[51] Int. Cl.[4] .......................... G02B 6/00; G01J 3/00
[52] U.S. Cl. .............................. 350/96.1; 350/96.28; 356/300
[58] Field of Search .............. 350/96.10, 96.15, 96.28; 356/300

[56] References Cited

U.S. PATENT DOCUMENTS

| | | |
|---|---|---|
| 2,807,976 | 10/1955 | Vossberg . |
| 3,183,295 | 5/1965 | Myles ........................... 350/96.1 X |
| 3,323,410 | 10/1963 | Waters . |
| 3,332,315 | 7/1967 | Wilks ........................... 350/96.1 X |
| 3,370,502 | 2/1968 | Wilks ........................... 350/96.1 X |
| 3,486,829 | 12/1969 | Wilks ........................... 350/96.1 X |
| 3,628,867 | 12/1971 | Brady . |
| 3,669,545 | 6/1972 | Gilby ............................... 356/320 |
| 4,136,960 | 1/1979 | Huang et al. . |
| 4,400,054 | 8/1983 | Biard et al. ...................... 350/96.15 |
| 4,602,869 | 7/1986 | Harrick ............................. 346/244 |
| 4,626,065 | 12/1986 | Mori ................................ 350/96.15 |

FOREIGN PATENT DOCUMENTS

| | | |
|---|---|---|
| 1158131 | 7/1969 | United Kingdom . |
| 1348462 | 3/1974 | United Kingdom . |
| 1463061 | 2/1977 | United Kingdom . |
| 2030724A | 4/1980 | United Kingdom . |
| 2119540 | 11/1983 | United Kingdom ............... 350/96.1 |
| 2148024A | 5/1985 | United Kingdom . |

OTHER PUBLICATIONS

Buck Scientific, IR/FT-IR-New Products Catalog.
Buck Scientific, I.R./F.T.I.R. Accessories and Instrumentation Guide, Mar. 1986.
Products Catalog Spectra-Tech, Inc.
1987 Products Catalog, SPECAC, Ltd.
N. J. Harrick, Prism Liquid Cell, Applied Spectroscopy, vol. 37, No. 6 (1983).
R. G. Messerschmidt, "Internal Reflection Element Design for High Optical Throughput in FT-IR" (unpublished).
Korolev et al, "Universal Attachment for Performing Investigations by the Method of Disruptive Multiple Total Internal Reflection", 7-1974, *Prib. & Tekh. Eksp.* (USSR), vol. 17, No. 4, pt. 2, pp. 1232-1234.
N. J. Harrick, Internal Reflection Spectroscopy, 1967, pp. 196 and 206.

Primary Examiner—John Lee
Assistant Examiner—John Ngo
Attorney, Agent, or Firm—Kenyon & Kenyon

[57] ABSTRACT

A multiple internal reflectance crystal has a sample surface and a bottom surface and reflective beveled ends such that energy may enter normal to the bottom surface, reflect off one beveled end to the bottom surface, from the bottom surface to the top surface, down the length of the crystal, and exit the crystal normal to the bottom surface by reflecting off of another beveled end. The crystal may be optically linked with light pipes and positioned at a location remote from the source and receiver of energy.

11 Claims, 2 Drawing Figures

MULTIPLE INTERNAL REFLECTANCE SPECTROSCOPY SYSTEM

BACKGROUND OF THE INVENTION

1. Field of the Invention.

The present invention relates to the structure of a multiple internal reflectance crystal.

2. Description of Related Art.

Several structures for multiple internal reflectance crystals are known in the art. For example, radiant energy, such as infrared energy, may enter a crystal through a first beveled face so as to reflect off a first side. The energy reflects between the first side and a second side down the length of the crystal by the physical phenomenon of total internal reflection. A sample that is placed against either the first or second side of the crystal selectively absorbs different frequencies of energy. The energy that is not absorbed exits the crystal through a second beveled face to a detector that measures the distribution of energy absorbed by the sample so as to obtain its spectrum.

The depth to which the incident energy penetrates a sample depends on the refractive index of the sample and the multiple reflectance crystal, as well as the angle of incidence at which the energy reflects off of the side of the crystal that is in contact with the sample. The angle of incidence may be changed by changing the angle at which energy enters the crystal, henceforth referred to as the entrance angle. A multiple internal reflectance crystal, however, introduces chromatic aberration into the resulting distribution of energy if the incident energy is not normal to the surface of an entrance face of the crystal. Therefore, each desired angle of incidence requires a separate crystal having an entrance face with an appropriate bevel angle. Changing crystals, however, consumes much time in realigning the transfer optics so that the energy both enters and exits the new crystal normal to the entrance face.

Another form of multiple internal reflectance crystal uses a prism to reflect the incident energy to the multiple internal reflectance crystal. The radiant energy is introduced normal to an entrance face of the prism. The prism reflects the radiant energy into the multiple reflectance crystal so that the radiant energy internally reflects off of a side of the crystal in contact with the sample. The prism, however, must be in physical contact with a lower surface of the multiple internal reflectance crystal to avoid introducing chromatic aberrations into the incident energy because the beam of radiant energy is not introduced into the crystal normal to the bottom face of the crystal. Radiant energy is collected from the crystal and prism in a similar manner. A prism-type crystal design does not require realigning optical components for each entrance angle. The requirement that the prism be in physical contact with the multiple internal reflectance crystal, however, means that the entrance face of the prism is always located a relatively short distance below the entrance face of the crystal. For many applications the multiple internal reflectance crystal must be located at a substantial distance from the source and receiver of the radiant energy. It is often difficult to introduce and collect radiation from the prism because the energy must enter the crystal substantially parallel to the crystal only a small distance below the sample surface.

Many other designs for multiple internal reflectance crystals are known in the art. No known design, however, permits any one of several multiple internal reflectance crystal having differing angles of incidence to be positioned at a location that is remote from a source and receiver of radiant energy without realigning the transfer optics. Moreover, most known crystal designs can receive the radiant energy only over a relatively small entrance angle.

SUMMARY OF THE INVENTION

The present invention employs a multiple internal reflectance crystal wherein radiant energy forms an optical path between a first side and a second side and the first side and a beveled edge. The radiant energy enters or exits the reflectance crystal normal to the first side and reflects off the beveled edge. In the preferred embodiment, first and second reflective beveled edges are located at ends of the crystal opposite a first side, henceforth referred to a the bottom side, so that the incident energy reflects from the first beveled edge back to the bottom side and off the bottom side to the second side, henceforth referred to as the sample side. The energy proceeds down the length of the crystal by undergoing multiple internal reflections between the surface and bottom sides until finally reflecting off of the second beveled edge and exiting the crystal normal to the bottom side. Thus, the alignment of the transfer optics does not change for each new crystal having a different entrance angle because the entrance face of the crystal is not beveled.

The multiple internal reflectance crystal of the present invention may be positioned an arbitrarily large distance away from the source and receiver of the radiant energy so long as the energy enters the crystal normal to the bottom side. Light pipes may be used to position the multiple internal reflectance crystal further from a source and receiver of the radiant energy, such as a spectrophotometer.

The multiple internal reflectance crystal of the present invention has a relatively large entrance and exit aperture. The entrance aperture is defined as a cross sectional area of an energy beam that can be accepted by the crystal. The entrance aperture for the multiple internal reflectance crystal of the present invention is represented by a different mathematical equation which obtains greater efficiency at different entrance angles than many other crystal designs. Thus, the multiple internal reflection crystals of the present invention can obtain a high input efficiency over a wide range of entrance angles. The multiple internal reflection crystal of present invention also has a large, unobstructed sample side which is ideal for many spectroscopic applications, especially FT-IR spectroscopy.

DESCRIPTION OF THE PREFERRED EMBODIMENTS

Figure 1:
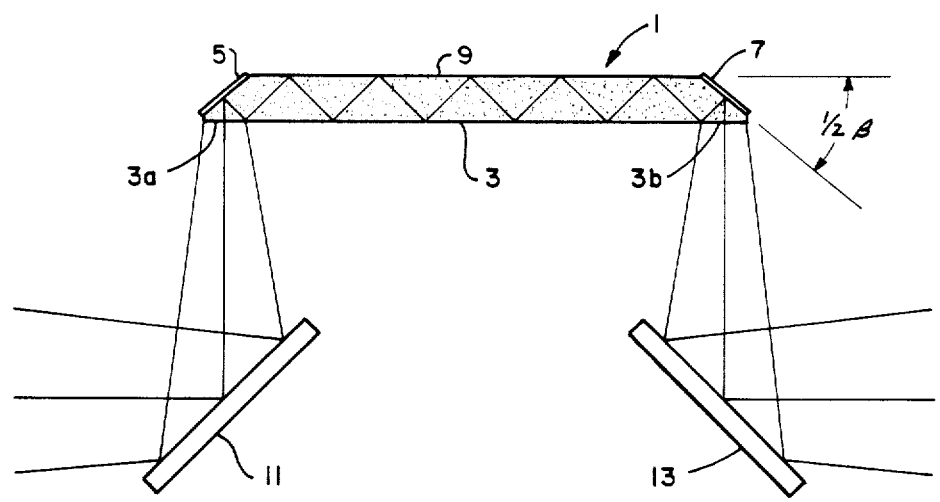
FIG. 1 show the preferred embodiment of a multiple internal reflectance crystal according to the present invention.

Referring to FIG. 1, the multiple internal reflectance crystal of the present invention is represented generally by reference numeral 1. Crystal 1 has a bottom side 3 and first and second beveled edges 5 and 7. Radiant energy is received into the crystal normal to an entrance face 3a that is contiguous with bottom side 3 of crystal 1. The radiant energy reflects off of first beveled edge 5 to bottom side 3, and from bottom side 3 to sample side 9. The radiant energy undergoes multiple internal reflections off the sample side and bottom side of the crystal. After a predetermined number of internal reflections, the energy reflects off second beveled edge 7 and is discharged from the crystal normal to an exit face 3b that is contiguous with bottom side 3. It is preferred that both first beveled edge 5 and second beveled edge 7 have a reflective coating. A sample is placed on sample side 9 so that some enegy is absorbed by the sample each time the radiant energy reflects from sample side 9. Mirrors 11 and 13 optically link crystal 1 with a source and receiver of radiant energy such as a spectrophotometer.

Figure 2:
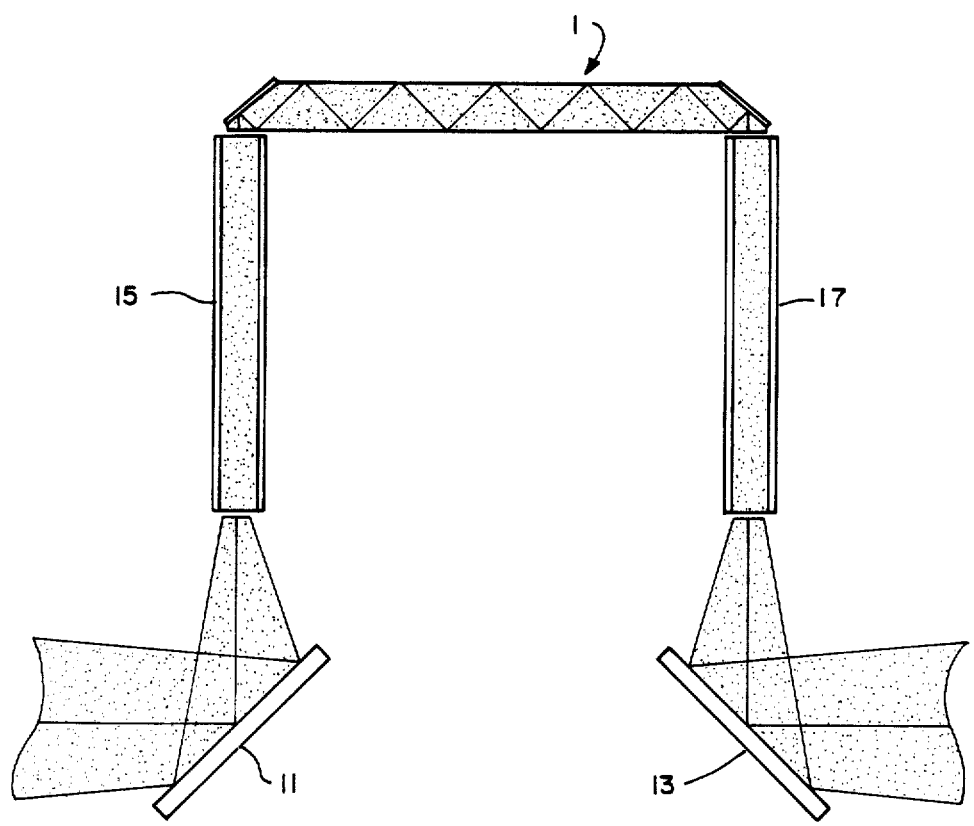
FIG. 2 shows the multiple internal reflectance crystal of FIG. 1 used in conjunction with light pipes to position the crystal away from the source and receiver of radiant energy.

FIG. 2 shows an arrangement of light pipes suitable for linking the multiple internal reflection crystal of the present invention to the sample compartment of a spectrophotometer. Light pipe 15 directs incident radiant energy from mirror 11 so as to be introduced into the crystal at the entrance face of Crystal 1. Likewise, light pipe 17 directs radiant energy discharged through the exit face of crystal 1 to mirror 13. It is to be appreciated, however, that the light pipes could have a variety of shapes; for example, either conically tapered or rectangularly tapered light pipes could condense the energy beam. It is a feature of the multiple internal reflectance crystal of the present invention that light pipes may easily and practically form an optical link between the multiple internal reflectance crystal and the source and receiver of the radiant energy. The multiple internal reflectance crystal of the present invention may be positioned at an arbitrarily great distance from the source and receiver of the radiant energy by merely cutting the light pipes to the proper length rather than by grinding special curved optics to produce the desired focal length. Moreover, light pipes may be sealed to the evacuated sample compartment of an infrared spectrophotometer so that attenuating ambient air is not present in the path of the energy beams.

A benefit of the reflectance crystal shown in FIGS. 1 and 2 is that the crystal accepts a wider entrance and exit beam than conventional multiple internal reflectance crystals. The aperture of an internal reflection crystal is defined as the cross sectional area of an energy beam that can be conducted down the length of the crystal at the desired angle of incidence. If the cross sectional area of the entrance beam is larger than the crystal, the optical throughput increases linearly with the area of the crystal aperture. The effective aperture is governed by the following equations:

$$A = 2t\beta,$$

where $\beta < 60°$;
and $$A = t \cot (\beta/2),$$

where $\beta \geq 60°$
where $\beta$, shown in FIG. 1, represents twice the bevel angle as measured relative to the sample surface.

While it is possible to obtain higher efficiencies for entrance angles greater than 60° with other types of multiple internal reflectance crystals, the aperture response of a present invention is sufficient for most applications. For example, the present invention has been successfully used to analyze skin samples, both in vivo and ex vivo.

It is to be appreciated, of course, that the greater entrance angle, constant alignment of transfer optics, and other utilities of the present invention may be separately obtained for receiving energy into an internal reflectance crystal or for discharging energy from an internal reflectance crystal. Likewise, neither the bottom side of the reflectance crystal nor the top side of the reflectance crystal need be flat, continuous surfaces, and the entrance and exit faces need not be contiguous with the bottom surface. The advantage inherent in the present invention may be obtained by reflecting radiant energy off a beveled reflective surface that is at an acute angle relative to an internally reflective surface other than the sample surface, whether or not that surface is contiguous, or even parallel, to the entrance face or exit face of the crystal.

The principles, preferred embodiments and modes of operation of the present invention have been described in the foregoing specification. The invention which is intended to be protected herein should not, however, be construed as limited to the particular forms described, as these are to be regarded as illustrative rather than restrictive. Variations and changes may be made by those skilled in the art without departing from the spirit of the present invention. Accordingly, the foregoing detailed description should be considered exemplary in nature and not as limiting to the scope and spirit of the invention set forth in the appended claims.

What is claimed is:

1. An internal reflectance spectroscopy system, especially for the spectroscopic analysis of a surface, wherein radiant energy undergoes internal reflection at a constant angle of incidence and reflection in an internal reflectance crystal, comprising:
    a first side;
    a second side;
    a first beveled edge oriented at an acute angle with respect to said first side;
    a second beveled edge on said crystal being oriented at an acute angle to said first side;
    first radiation transfer means for condensing a beam of the radiant energy into the crystal to form an optical path extending directly through said first side to said first beveled edge, from said beveled edge directly back to said first side, from said first side directly to said second side, from said second side directly to said first side, from said first side directly to said second beveled edge, and from said second beveled edge directly through said first side, said first radiation transfer means defining an entrance for the radiant energy; and
    second radiation transfer means for receiving a diverging beam of the radiant energy that is reflected from said second beveled edge through said first side of the crystal, said second radiation transfer means defining an exit for the radiant energy.

2. An internal reflectance spectroscopy system as claimed in claim 1, wherein said first and second beveled edges are separated by a predetermined distance such that the radiant energy internally reflects in said crystal a plurality of times between said first and second sides.

3. An internal reflectance spectroscopy system as claimed in claim 1 wherein said first and second beveled edges are coated with a material that reflects the radiant energy.

4. An internal reflectance spectroscopy system as claimed in claim 1, wherein:
said first radiation transfer means comprises a first light pipe for directing the radiant energy through said surface to said first beveled edge; and
said second radiation transfer means comprises a second light pipe for receiving said diverging beam of radiant energy reflected from said second beveled edge through said first side.

5. An internal reflectance spectroscopy system as claimed in claim 4, wherein:
said first light pipe has tapered sides that condense the radiant energy; and
said second light pipe has tapered sides that diverge the radiant energy.

6. An internal reflectance spectroscopy system as claimed in claim 4, wherein said first and second light pipes are purged of gasses that attenuate the radiant energy.

7. An internal reflectance spectroscopy system as claimed in claim 1, wherein said first side and said second side are parallel.

8. An internal reflectance spectroscopy system as claimed in claim 7, wherein:
said first side comprises a flat, contiguous surface; and
said second side comprises a flat, contiguous surface.

9. A method of reflecting radiant energy in an internal reflectance spectroscopy system for use in spectroscopy, especially in the spectroscopic analysis of a surface, wherein radiant energy undergoes internal reflection at a constant angles of incidence and reflection in an internal reflectance crystal, comprising the steps of:
receiving the radiant energy at an entrance;
condensing the radiant energy from the entrance into the crystal through a first side to a first beveled edge;
directing the radiant energy from said first beveled edge directly to said first side;
reflecting the radiant energy from said first side directly to a second side of said crystal;
reflecting the radiant energy from said second side directly to said first side;
reflecting the radiant energy from said first side directly to a second beveled edge, said second beveled edge being oriented at an acute angle relative to said first side;
directing the radiant energy from said second beveled edge directly through said first side to form a diverging beam of radiant energy; and
discharging the radiant energy forming said diverging beam to an exit.

10. A method as claimed in claim 9, wherein:
the radiant energy enters the crystal normal to said first side; and
the radiant energy is discharged from the crystal normal to said first side.

11. A method as claimed in claim 9, further comprising the steps of reflecting the radiant energy between said first and second sides a plurality of times.

* * * * *

Disclaimer and Dedication 4,730,882—Robert G. Messerschmidt, Westport, Conn. MULTIPLE INTERNAL REFLECTANCE SPECTROSCOPY SYSTEM. Patent dated March 15, 1998. Disclaimer and Dedication filed June 15, 2001, by the assignee, Spectra-Tech, Inc.

Hereby disclaims and dedicates to the Public all claims and entire term of said patent.
*(Official Gazette, August 14, 2001)*